United States Patent [19]

Rumpf et al.

[11] Patent Number: 5,453,256

[45] Date of Patent: Sep. 26, 1995

[54] CATALYTIC REACTOR

[75] Inventors: Günter Rumpf, Weilrod; Peter Schlau, Frankfurt, both of Germany

[73] Assignee: Mannesmann Aktiengesellschaft, Dusseldorf, Germany

[21] Appl. No.: 224,801

[22] Filed: Apr. 8, 1994

[30] Foreign Application Priority Data

Apr. 8, 1993 [DE] Germany .......................... 43 12 100.4

[51] Int. Cl.$^6$ ....................................... B01J 8/02
[52] U.S. Cl. .......................... 422/211; 422/241; 422/307
[58] Field of Search ..................... 422/140, 241, 422/201, 244, 261, 307, 211; 122/4 D; 392/394, 399

[56] References Cited

U.S. PATENT DOCUMENTS

| | | | |
|---|---|---|---|
| 457,362 | 8/1891 | Mitchell | .................................. 392/394 |
| 2,536,307 | 1/1951 | Olson | .......................................... 196/52 |
| 3,648,018 | 3/1972 | Cheng et al. | ............................ 392/394 |
| 3,864,088 | 2/1975 | Delin et al. | ........................... 392/399 X |

*Primary Examiner*—Timothy M. McMahon
*Attorney, Agent, or Firm*—Cohen, Pontani, Lieberman, Pavane

[57] ABSTRACT

A catalytic reactor in which liquid media can be continuously introduced, evaporated and fed to catalytic reactions, wherein the reactor space is formed by a tubular reactor casing which is open at one end and can be closed by a reactor lid having a through-opening. A pipe acting as evaporator stage is arranged so as to extend from the region of the through-opening until deep in the reactor space and is provided with a baffle and a baffle holder at the end extending into the reactor space. The rest of the reactor space is filled at least partially with catalyst and forms a catalysis stage. The pipe, baffle and baffle holder are made of ceramic material and the pipe and baffle holder are constructed as a single piece.

10 Claims, 1 Drawing Sheet

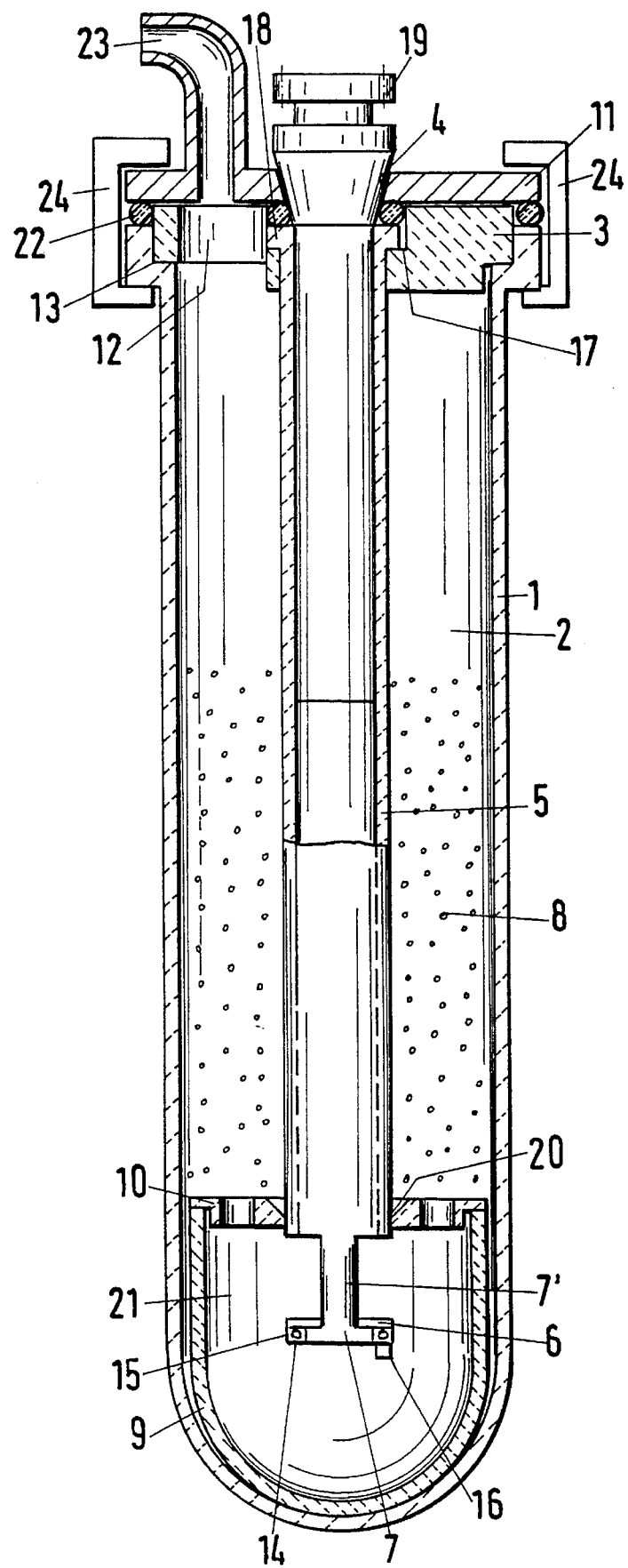

CATALYTIC REACTOR

BACKGROUND OF THE INVENTION

1. Field of Invention

The invention is directed to a catalytic reactor in which liquid media can be continuously introduced, evaporated and fed to catalytic reactions. A reactor space is formed by a tubular reactor casing which is open at one end and can be closed by a reactor lid having a through-opening. A pipe acting as an evaporator stage is arranged so as to extend from the region of the through-opening in the lid until deep in the reactor space and is provided with a baffle and a baffle holder at the end extending into the reactor space. The rest of the reactor space is filled at least partially with catalyst and forms a catalysis stage.

2. Description of the Prior Art

Catalytic reactors of the above type are often used in the field of technical analysis. Liquid media serving, for example, as carriers for substances to be subjected to a catalytic reaction with or without the liquid medium evaporated along with them are introduced into the reactor.

Such catalytic reactors can also often be used for analysis or dissociation of dissolved substances. In so doing, the liquid medium, including the contents dissolved therein, is evaporated suddenly in that it is dripped through a pipe inserted into the reactor space onto a baffle plate which is preheated to temperatures of several hundred to more than a thousand degrees. The suddenly evaporated medium exits the pipe in the region of the baffle holder and is then fed to the catalyst. In order to maintain an undisturbed transition from the liquid phase to the steam phase and to feed the evaporated medium to the catalyst as uniformly as possible, it is known to arrange the outlet of the pipe such that it opens in the region of the baffle and baffle holder into a bowl-shaped sieve element which is closed by a sieve cover. The evaporated medium can now also expand in this space in a correspondingly sudden manner, whereupon it diffuses through the sieve cover into the catalysis zone. The remaining reactor space is accordingly at least partially filled with the catalyst. The evaporated medium diffuses through this catalyst or, when a pressure gradient is introduced along the catalytic path, is "sucked through" the catalyst. The catalytic path lets out through a corresponding opening with a retainer ring and passes outward through another opening in the reactor lid.

In a known construction, the reactor is made of ceramic material at least in part, i.e. in substantial regions of the reactor casing. The baffle holder is arranged at the pipe and is commonly made of metallic material.

A disadvantage in the prior art is that the use of different materials precisely in the region in which the sudden evaporation occurs leads to mechanical stresses which considerably shorten the life of the reactor. In addition, the mechanical interconnection of metallic and ceramic parts is disadvantageous and costly in terms of manufacturing technique.

SUMMARY OF THE INVENTION

Proceeding from a catalytic reactor of the known type, the present invention has the object of providing a catalytic reactor that is stable under high temperatures, free of stresses and simple to manufacture as a whole.

Pursuant to this object, and others which will become apparent hereafter, one aspect of the present invention resides in a catalytic reactor in which the pipe, baffle and baffle holder are made of ceramic material and the pipe and the baffle holder are constructed as one piece. This offers the advantage that the pipe and baffle holder need no longer be assembled. Due to the fact that the baffle is formed of ceramic material, it can be inserted in the baffle holder, which is likewise ceramic, without being subjected to stresses due to changes in temperature.

Pursuant to a further embodiment of the invention a bowl shape member is arranged at the bottom end of the reactor casing and is covered by a perforated plate. The pipe projects into the bowl-shaped member in the region of the baffle holder. It is preferable to construct the bowl-shaped member and perforated plate from a ceramic material.

In another embodiment of the invention a retainer ring can be inserted below the reactor lid with a partial positive-locking engagement so that the pipe is secured in a corresponding manner. The retainer ring is also made of ceramic material. Accordingly, the entire arrangement has very high thermomechanical stability, which considerably increases the life of the reactor.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWING

The single figure shows a cross section through a catalytic reactor pursuant to the present invention.

DETAILED DESCRIPTION OF THE PREFERRED EMBODIMENTS

The reactor itself has a reactor casing 1 with an open upper end which can be closed by a reactor lid 11 and a closed lower end. The lid 11 is preferably made of glass. The reactor casing 1 encloses and forms a reactor space 2. In the assembled state, a pipe 5 projects into the reactor space and is held at its end in the vicinity of the reactor lid by a retainer ring 3. After attaching and securing the reactor lid 11, the pipe 5 and retainer ring 3 are secured and held in a positive connection. The reactor lid is secured via clamping members 24. However, if the reactor is accommodated in a furnace, the reactor may be held via holding members which are arranged inside the furnace and embrace the reactor lid at the same time. In general, it is important that seals 22 are held in the desired position and pressed down so as to ensure the necessary tightness and to ensure that the flanges 18 of the pipe 5 are pressed into a step 17 of the retainer ring 3 in a positive-locking manner so that the pipe is held securely. The reactor lid 11 has a through-opening 4 through which the pipe 5 extends. In order to ensure this secure holding after the reactor is assembled, the reactor casing 1 is provided at its open end with a circumferential step 13 in which the retainer ring 3 is inserted. The retainer ring 3 itself has an opening for receiving and securing the pipe 5 which extends through this opening. The opening is provided with the step 17. At its end which is held in the retainer ring 3, the pipe 5 has a collar-like pipe flange 18 which is inserted into the step 17 of the retainer ring 3. The entire arrangement is secured by sealing rings 22 after the reactor lid 11 is placed on top, so that the pipe 5 is secured in a central position with respect to the reactor cross section. It can be seen from the sectional view along the longitudinal axis that the step 13 and the pipe flange 18 and the step 17 extend circumferentially and are symmetrical with respect to rotation. The pipe 5 also has a pipe connection 19 at its end situated outside the reactor in the assembled state.

A bowl-shaped member 9, which is covered by a perforated plate 10, is arranged inside the reactor at the closed end, i.e. at the bottom. The perforated plate has a central opening 20. The pipe 5 extends through the opening 20 into an evaporator space 21 formed by the bowl-shaped member 9. A baffle 6 is provided in the region of the open end of the pipe and is held at an appropriate distance from the open end of the pipe by the baffle holder 7. The baffle holder 7 holds the baffle 6 in a position relative to the end of the pipe so that the baffle surface facing the end of the pipe is aligned parallel to the pipe cross section. The baffle holder 7 holds the baffle 6 at an appropriate distance from the open end of the pipe, as already mentioned, via webs 7'. This portion of the reactor in the region of the bowl-shaped member 9 is the so-called evaporator stage, and is covered by the perforated plate 10, as mentioned above. The perforated plate 10 is provided with a plurality of holes which allow the medium in the form of steam to enter the rest of the reactor space 2. However, the holes are so small that the catalyst 8, which is generally in the form of powder or balls, does not penetrate into the evaporator space 21.

The rest of the reactor space 2 accordingly forms the so-called catalysis stage which is filled at least partially with the catalyst 8. In the region of the baffle holder 7, i.e., more particularly in the region of the baffle 6, an annular support 15 is provided which engages annularly around the baffle holder 7 in this region. A resistive heating device 14 which can heat the baffle 6 to suitable evaporation temperatures is arranged inside the support 15. Electrical lines of the heating device are guided out of the reactor in the region of pipe 5. A temperature sensor 16, by means of which the temperature of the baffle can be monitored and regulated, is arranged between the support 15 and baffle holder 7. A conventional heating arrangement arranged outside the casing can also be used to heat the evaporator space.

The reactor functions in the following manner:

The liquid medium is introduced into the reactor via the pipe connection 19 and drips through the pipe 5 into the evaporator stage of the reactor. In so doing, the liquid medium drips on the hot baffle plate 6 and evaporates into the corresponding evaporator space 20 of the bowl-shaped member 9. The evaporated medium now passes through the perforated plate 10 into the catalysis stage 8 through which it diffuses and can be carried off again e.g. via the through-opening 12 of the retainer ring 3 and via the pipe flange 23 in the reactor lid 11. The pipe 5, baffle 6 and baffle holder 7 are made of ceramic material and the pipe 5 and baffle holder 7 are constructed in one piece. The retainer ring 3, bowl-shaped member 9 and perforated plate 10 are advisably also made of ceramic material. Accordingly, all zones of the entire reactor arrangement have stability under high temperatures and are free of stresses and extremely simple to manufacture as a whole.

The invention is not limited by the embodiments described above which are presented as examples only but can be modified in various ways within the scope of protection defined by the appended patent claims.

We claim:

1. A catalytic reactor in which liquid media can be continuously introduced, evaporated and fed to catalytic reactions, comprising: a tubular reactor casing that forms a reactor space and is open at one end; a reactor lid for closing the open end of the reactor casing, the reactor lid having a through-opening; a pipe acting as an evaporator stage arranged so as to extend from the through-opening into the reactor space; a baffle holder arranged at an end of the pipe extending into the reactor space, the remaining reactor space being at least partially filled with catalyst and forming a catalysis stage, the pipe, the baffle and the baffle holder being made of ceramic material, and the pipe and the baffle holder being constructed as a single homogeneous piece; and means for heating the lower part of the reactor casing and the baffle and further comprising a retainer ring insertable into the reactor casing so as to secure the pipe in the reactor below the reactor lid and so as to form a partial positive-locking connection after the reactor is closed by the reactor lid.

2. A catalytic reactor according to claim 1, wherein the reactor casing has a bottom end opposite the open end, and further comprising a bowl-shaped member arranged at the bottom end of the reactor casing, and a perforated plate arranged so as to cover the bowl-shaped member, the pipe being arranged to project into the bowl-shaped member in the region of the baffle holder.

3. A catalytic reactor according to claim 2, wherein the bowl-shaped member and the perforated plate are made of ceramic material.

4. A catalytic reactor according to claim 1, wherein the reactor lid is made of glass.

5. A catalytic reactor according to claim 1, wherein the retainer ring is constructed so as to be insertable into a circumferential step at the open end of the reactor casing, the pipe being secured centrally relative to the reactor cross section.

6. A catalytic reactor according to claim 5, wherein the retainer ring is an intermediate lid which is insertable below the reactor lid, the retainer ring having a through-opening in a region between the pipe, which is secured in an assembled state of the reactor, and the reactor casing, through which opening the reactor can be filled with the catalyst before the reactor lid closes the reactor.

7. A catalytic reactor according to claim 1, wherein the heating means includes a resistive heating element arranged at the baffle holder, the heating element having electrical lines that are guided out of the reactor in a region of the pipe.

8. A catalytic reactor according to claim 7, and further comprising an annular support connected with the baffle holder so as to embrace it annularly, the heating element being arranged in the annular support.

9. A catalytic reactor according to claim 8, and further comprising a temperature sensor arranged near the baffle holder and the annular support.

10. A catalytic reactor according to claim 1, wherein the retainer ring is made of ceramic material.

* * * * *